(12) United States Patent
Gregory et al.

(10) Patent No.: US 6,335,442 B1
(45) Date of Patent: Jan. 1, 2002

(54) PHTHALOCYANINES

(75) Inventors: Peter Gregory, Bolton; Stephen James Reynolds, Manchester, both of (GB)

(73) Assignee: Avecta Limited, London (GB)

( * ) Notice: Subject to any disclaimer, the term of this patent is extended or adjusted under 35 U.S.C. 154(b) by 0 days.

(21) Appl. No.: 08/794,759

(22) Filed: Feb. 3, 1997

(30) Foreign Application Priority Data

Feb. 3, 1996 (GB) .................................................. 9602095

(51) Int. Cl.$^7$ ............................ C07D 259/00; C07F 1/12; C07F 3/02; C07F 1/04
(52) U.S. Cl. ............................ 540/122; 540/139; 540/140
(58) Field of Search .................................. 540/122, 139, 540/140, 136

(56) References Cited

FOREIGN PATENT DOCUMENTS

| EP | 0 155 780 A3 | 9/1985 |
|---|---|---|
| EP | 0 155 780 A2 | 9/1985 |
| EP | 0 484 018 A2 | 5/1992 |
| EP | 0 484 027 A1 | 5/1992 |
| EP | 0 638 614 A1 | 2/1995 |
| FR | 816859 | 10/1937 |
| JP | 61-198241 | 9/1986 |
| JP | 07-179042 | * 7/1995 |

OTHER PUBLICATIONS

Umehara et al, Chemical Abstract 1995:823631 (for JP 07–179042).*

Pauling, General Chemistry, 2nd ed,. W. H. Freeman and Company, 1953, 192–211.*

* cited by examiner

*Primary Examiner*—John M. Ford
(74) *Attorney, Agent, or Firm*—Pillsbury Winthrop LLP

(57) ABSTRACT

Phthalocyanine compounds substituted by from 1 to 8 substituents of formula (—O—R—O—) wherein R is a 1,2-arylene group are provided. Preferably, the phthalocyanine compounds are substituted by catechol. Additional substituents which may be present include hydrocarlyloxy, hydrocarbylthio, halogen and sulphonic acid or a salt thereof.

19 Claims, No Drawings

PHTHALOCYANINES

This invention relates to phthalocyanines and more particularly to substituted phthalocyanines exhibiting strong absorption maxima in the near infra-red region of the electromagnetic spectrum, for example in the region between 750 and 900 nm.

According to the invention, there are provided phthalocyanine compounds of the formula:

$$M_kPc(-O-R-O-)_x(-YR^1)_y(-Z)_m(-SO_3A)_n \quad (1)$$

wherein $M_kPc$ is a phthalocyanine nucleus of the formula:

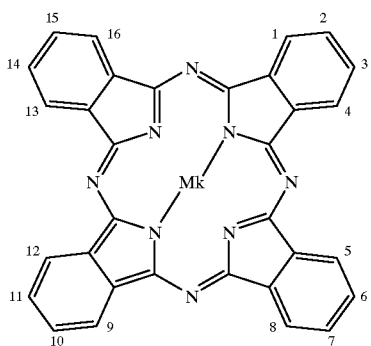

(2)

in which M represents a metal atom, a halogeno-metal group, an oxy-metal group or hydrogen and k is the inverse of half the valency of M;

R represents a substituted or unsubstituted 1,2-arylene group;

Y represents oxygen or sulphur;

$R^1$ represents a substituted or unsubstituted hydrocarbyl group;

Z represents a halogen or hydrogen;

A represents hydrogen, a metal or substituted or unsubstituted ammonium;

x represents an integer from 1 to 8;

y represents an integer from 0 to 14;

m represents an integer from 0 to 14;

n represents an integer from 0 to 32;

the sum of 2x, y and m not exceeding 16, and the groups or atoms $-O-R-O-$, $-YR^1$ and Z are attached to the peripheral carbon atoms numbered 1 to 16 in Formula 2, with the proviso that when n is zero, at least one 1,2-arylene group represented by R carries at least one alkyl group containing at least four carbon atoms.

As indicated by Formula 2 above, the phthalocyanine nucleus of the compounds of the invention may be metal-free or may contain a complexed metal, halogeno-metal or oxy-metal, that is to say it may carry two hydrogen atoms at the centre of the nucleus or it may carry one or two metal atoms, halogeno-metal groups or oxy-metal groups complexed within the centre of the nucleus. Where a metal atom, halogeno-metal or oxy-metal group is complexed within the centre of the nucleus, the atom or group may be mono or divalent. Where an ordinarily trivalent or higher valency metal is present, the valency above 2 is satisfied by one or more halogen or oxy groups. Halogeno-metal groups include fluoro-metal, bromo-metal, iodo-metal and particularly chloro-metal groups. Oxy-metal groups include metal compounds with one or more of divalent oxygen and monovalent oxygen-containing groups, for example, hydroxy groups, alkoxy, especially $C_{1-4}$ alkoxy, groups and aryloxy, especially phenoxy and naphthoxy, groups. The alkoxy and aryl oxy groups may be unsubstituted or may be substituted by one or more substituents selected from the list of substituents for R and $R^1$ given below. Examples of suitable metals, halogeno-metals and oxy-metals include lithium, sodium, copper, nickel, zinc, manganese, iron, chloro-iron, chloro-aluminium, tin, lead, vanadyloxy and titanyloxy.

Optionally substituted 1,2-arylene groups which may be represented by R include naphthylene and especially phenylene groups. The value of x is preferably 4 or 8.

Optionally substituted hydrocarbyl groups which may be represented by $R^1$ include optionally substituted alkyl groups and particularly optionally substituted aryl groups, for example naphthyl and especially phenyl groups. The preferred value of y is in the range from 0 to 8.

When either or both of R and $R^1$ are substituted, the substituents may be one or more substituents selected from the group consisting of $C_{1-20}$-alkyl, $C_{1-20}$-alkoxy, $C_{2-20}$-alkenyl, $C_{1-20}$-alkylthiol, $C_{1-20}$-alkoxycarbonyl, hydroxy $C_{1-4}$-alkoxy, phenyl, benzyl, phenylthio, fluoro, chloro, bromo, $-CN$, $-NO_2$, $-CF_3$, $-COR^2$, $-COOR^2$, $-CONR^2R^3$, $-SO_2R^2$, $-SO_2NR^2R^3$, $NR^2R$ and $-OR^2$ in which $R^2$ and $R^3$ are each independently H, $C_{1-4}$-alkyl or phenyl. Preferred substituents for R include $C_{1-20}$-alkyl groups.

Halogen atoms which may be represented by Z include fluorine, bromine, iodine and, especially, chlorine. The preferred value of m is in the range from 0 to 8.

Metals which may be represented by A include alkaline earth metals, and, especially, the alkali metals. It is preferred that A is sodium or hydrogen.

When A represents substituted ammonium, the ammonium group is substituted by from 1 to 4 groups selected from up to $C_{18}$ alkyl groups, preferably up to $C_4$ alkyl groups; and phenyl groups. Each substituent may be further substituted by one or more substituents selected from the list of substituents for R and $R^1$, above.

Compounds of the invention containing $-SO_3A$ groups, which may be attached directly to the peripheral carbon atoms of the phthalocyanine nucleus and/or to the pendent organic groups R and $R^1$ are soluble in water.

In compounds of the invention which contain no sulphonic acid or sulphonate groups (n=0), at least one 1,2-arylene group represented by R carries at least one alkyl group containing at least four carbon atoms so as to provide solubility in organic liquids. Suitable alkyl groups may contain from 4 to 20, preferably from 4 to 12 and especially from 4 to 8 carbon atoms. Preferred alkyl groups include branched alkyl groups, especially tertiary alkyl groups such as t-butyl and t-octyl. For maximum solubility, it is preferred that each 1,2-arylene group carries at least one alkyl group having at least four carbon atoms.

It is preferred that the solubility of the sulphonate-free phthalocyanines of the invention in organic liquids is at least 3%. Preferred organic liquids are selected from aliphatic and aromatic hydrocarbons, ethers, ketones, chlorinated aliphatic and aromatic hydrocarbons, amides and substituted amides. Specific examples of suitable organic liquids are tetrahydrofuran (THF), cyclohexanone, chloroform, toluene, dichloromethane (DCM) and dimethylformamide (DMF).

As specific examples of useful phthalocyanine compounds of Formula 1,there may be mentioned the compounds:

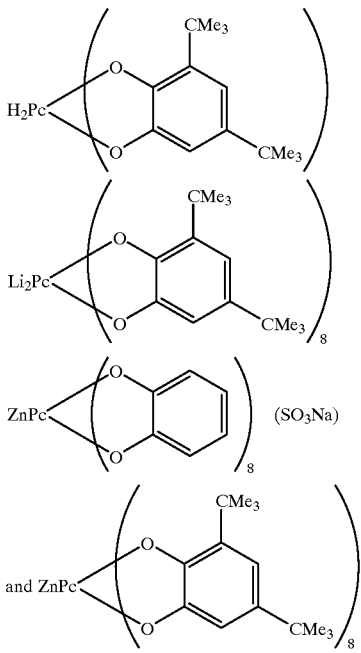

The phthalocyanine compounds of Formula 1 may be prepared by methods analogous to those used for the preparation of known phthalocyanine compounds. Thus, for example, an appropriately substituted phthalonitrile may be reacted with a metal or metal salt at an elevated temperature, optionally in an inert liquid and/or in the presence of catalytic materials. Sulphonation may then be effected if desired. Appropriately substituted phthalonitriles include phthalonitriles carrying two —ORO— substituents or carrying one —ORO— substituent and optionally one or two —YR$^1$ substituents. The phthalonitriles may themselves be prepared by reacting halogen-substituted phthalonitriles with catechols and, optionally, phenols.

The phthalocyanine compounds of the present invention are useful for absorbing electromagnetic radiation, especially in the near infra-red region of the spectrum, and they may be employed for this purpose in a variety of electronic devices. In this connection, it is to be noted that the optionally substituted catechol residues present in the compounds of Formula 1 provide a bathochromic effect of from 50 to 70 nm compared with the corresponding phenoxy-substituted phthalocyanines. In addition, the compounds can be used in security applications such as in printing currency or cheques, in ink jet printing, laser thermal printing, flash fusion of toners, optical data storage and as charge generating materials for laser thermal printing.

The invention is illustrated but not limited by the following Examples.

EXAMPLE 1

A mixture of catechol (20.64 g, 0.1875 mol), tetrachlorophthalonitrile (19.94 g, 0.075 mol) and potassium carbonate (25.91 g, 0.1875 mol) in DMF (200 ml) was heated and stirred at 100° C. for 1 hour and then allowed to cool. The resulting mixture was stirred in DCM (500 ml) and the undissolved solid collected by filtration. The solid was washed with water and then methanol (250 ml) and then dried in air to give the product (18.83 g, 74%) as an off-white solid, m.p. >250° C. The product was a di-catechol substituted phthalonitrile of the formula

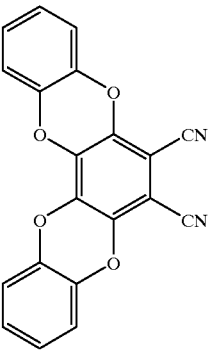

The di-catechol substituted phthalonitrile (5.1 g, 0.015 mol), zinc chloride (2.04 g, 0.015 mol), urea (0.24 g, 0.004 mol), ammonium molybdate tetrahydrate (0.03 g, 2.4×10$^5$ mmol) and 1,8-diazabicyclo[5.4.0]undec-7-ene (D.B.U. 2.28 g, 0.015 mol) were stirred at 240° C. under an atmosphere of nitrogen for 3 hours and then allowed to cool. The resulting slurry was stirred in DCM and the product was then fully precipitated by the addition of methanol and the solid collected by filtration and dried. The solvent treatment was repeated several times to remove impurities to leave an octa-catechol substituted zinc phthalocyanine of the formula:

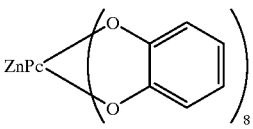

as a dull brown insoluble solid (5.46 g, 100%).

The phthalocyanine so obtained (4.27 g, 0.03 mol) was added to cooled 10% oleum (50 ml) under a stream of nitrogen and the resulting mixture was stirred for 2 hours. The mixture was then drowned out into ice/water and neutralised with caustic liquor. The resulting solution was filtered and the filtrate dried to a solid at 100° C. The resulting solid was dialysed to leave octa-catechol substituted zinc phthaiocyanine octasulphonate, sodium salt (5.68 g, 84.4%) as a dull brown solid; λmax 719 and 789 nm.

EXAMPLE 2

A mixture of 3,5-di<u>tert</u>butylcatechol (20 g, 0.09 mol), tetrachlorophthalonitrile (5.31 g, 0.02 mol) and potassium carbonate (12.43 g, 0.09 mol) in DMF (50 ml) was heated and stirred at 140° C. for 1 hour under an atmosphere of nitrogen and then allowed to cool. The resulting mixture was washed with methanol (2×400 ml) and then water (2×400 ml) and dried in air to give the product (9.05 g, 80%) as an off-white solid. The product was a di-3,5-di<u>tert</u>butylcatechol substituted phthalonitrile of the formula

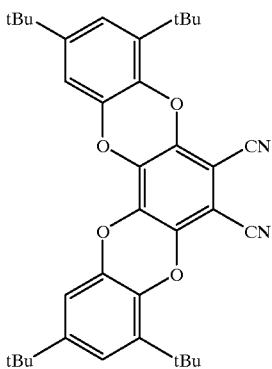

Lithium (0.08 g, 0.012 mol) and n-butanol (4 ml) were stirred at 120° C. under an atmosphere of nitrogen for 2 hr. The di-3,5-ditertbutyl catechol substituted phthalonitrile (2.12 g, 0.004 mol) and D.B.U. (0.57 g) were added and the resulting mixture stirred at 110° C. under an atmosphere of nitrogen for 4 h and then allowed to cool and drowned out into methanol. The resulting solid was collected by filtration and dried and then treated with methanol several times to remove to leave the lithium phthalocyanine of the formula:

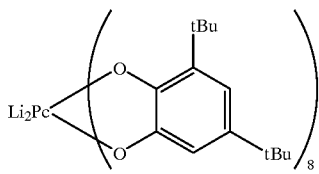

as a brown solid (0.74 g) $\lambda$max 832 nm.

A proportion of this solid (0.69 g), toluene (20 ml) and para-toluenesulphonic acid (0.23 g) were stirred for 3 h. The solvent was then removed in vacuo and the resulting solid was dissolved in DCM and reprecipitated with methanol. The solid was then washed with methanol to leave the corresponding metal-free phthalocyanine (0.27 g) as a brown solid; $\lambda$max 815 nm ($\epsilon$smax 152472).

EXAMPLE 3

Di-3,5-ditertbutylcatechol substituted phthalonitrile (5.6 g, 0.01 mol), zinc chloride (1.36 g, 0.01 mol), urea (0.15 g, 0.0025 mol), ammonium molybdate (VI) tetrahydrate (0.03 g, 2.4×10$^{-5}$ mmol) and D.B.U. (1.52 g, 0.01 mol) were stirred at 240° C. under an atmosphere of nitrogen for 2h and then allowed to cool and the resulting slurry was dissolved in DCM. The product was precipitated by the addition of methanol (400 ml), collected by filtration and dried. The solvent treatment was repeated several times to remove impurities leaving octa-(ditertbutylcatechol) substituted zinc phthalocyanine of the formula:

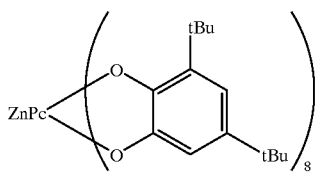

as a green/brown solid (3.71 g, 66%); $\lambda$max 795 nm ($\epsilon$max 62121).

What is claimed is:

1. A phthalocyanine compound of the formula:

$$M_kPc(-O-R-O-)_x(-YR^1)_y(-Z)_m(-SO_3A)_n \quad (1)$$

wherein $M_kPc$ is a phthalocyanine nucleus of the formula:

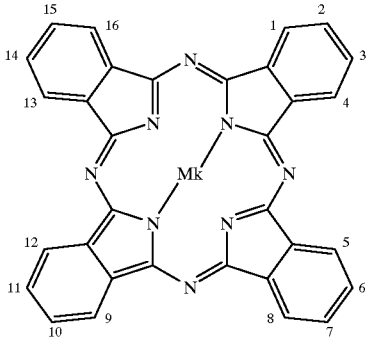

(2)

in which M is selected from the group consisting of hydrogen, lithium, sodium, copper, nickel, zinc, manganese, iron, chloro-iron, chloro-aluminum, tin, lead, vanadyloxy and titanyloxy, and k is the inverse of half the valency of M;

R represents an unsubstituted naphthylene or phenylene group, or a naphthylene or phenylene substituted by one or more substituents selected from the group consisting of $C_{1-20}$-alkyl, $C_{1-20}$-alkoxy, $C_{2-20}$-alkenyl, $C_{1-20}$-alkenyl, $C_{1-20}$-alkoxycarbonyl, hydroxy$C_{1-4}$-alkoxy, phenyl, benzyl, phenylthio, fluoro, chloro, bromo, —CN, —NO$_2$, —CF$_3$, —COR$^2$, —COOR$^2$, —CONR$^2$R$^3$, —SO$_2$R$^2$, —SO$_2$NR$^2$R$^3$, —NR$^2$R$^3$ and —OR$^2$ in which R$^2$ and R$^3$ each independently is —H, $C_{1-4}$-alkyl or phenyl;

Y represents oxygen or sulphur;

R$^1$ represents an unsubstituted alkyl, naphthyl or phenyl group, or an alkyl, naphthyl or phenyl group substituted by one or more substituents listed for the R group;

Z represents a halogen or hydrogen;

A represents hydrogen , alkaline earth metals, alkali metals, unsubstituted ammonium or ammonium substituted by from 1 to 4 substituents selected from the group consisting of $C_{1-18}$-alkyl and phenyl, each said substituent being optionally substituted by one or more substituents listed for the R group;

x represents an integer from 1 to 8;

y represents an integer from 0 to 14;

m represents an integer from 0 to 14;

n represents an integer from 0 to 32;

the sum of 2x, y and m not exceeding 16, the groups or atoms —O—R—O—, —YR$^1$ and Z are attached to the peripheral carbon atoms numbered 1 to 16 in Formula 2,and both of the O atoms in the —O—R—O— group are bound to adjacent carbon atoms in the phthalocyanine nucleus, with the proviso that when n is zero, at least one naphthylene or phenylene group represented by R carries at least one alkyl group containing at least four carbon atoms.

2. A phthalocyanine compound according to claim 1 wherein R is a phenylene group which is unsubstituted or is substituted by one or more $C_{1-20}$-alkyl groups.

3. A phthalocyanine compound according to claim 1 or claim 2 wherein x is 4 or 8.

4. A phthalocyanine compound according to claim 1 or 2 wherein y is in the range from 0 to 8.

5. A phthalocyanine compound according to claim 1 or 2 wherein m is in the range from 0 to 8.

6. A phthalocyanine compound according to claim 1 or 2 wherein A is sodium or hydrogen.

7. A phthalocyanine compound according to claim 1 or 2 wherein n is zero and each naphthalene or phenylene group represented by R carries at least one alkyl group having at least four carbon atoms.

8. A phthalocyanine compound according to claim 1 or claim 2 wherein $R^1$ is an unsubstituted naphthyl or phenyl group, or a naphthyl or phenyl group substituted by one or more substituents listed in claim 1 for the R group.

9. A phthalocyanine compound according to claim 1, wherein M is selected from the group consisting of hydrogen, lithium and zinc.

10. A phthalocyanine compound of the formula

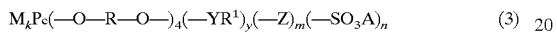

$$M_kPc(-O-R-O-)_4(-YR^1)_y(-Z)_m(-SO_3A)_n \quad (3)$$

wherein $M_kPc$ is selected from the group consisting of hydrogen, lithium, sodium, copper, nickel, zinc, manganese, iron, chloro-iron, chloro-aluminum, tin, lead, vanadyloxy and titanyloxy, and k is the inverse of half the valency of M;

R represents an unsubstituted naphthylene or phenylene group, or a naphthylene or phenylene substituted by one or more substituents selected from the group consisting of $C_{1-20}$-alkyl, $C_{1-20}$-alkoxy, $C_{2-20}$-alkenyl, $C_{1-20}$-alkylthiol, $C_{1-20}$-alkoxycarbonyl, hydroxy$C_{1-4}$-alkoxy, phenyl, benzyl, phenylthio, fluoro, chloro, bromo, $-CN$, $-NO_2$, $-CF_3$, $-COR^2$, $-COOR^2$, $-CONR^2R^3$, $-SO_2R^2$, $-SO_2NR^2R^3$, $-NR^2R^3$ and $-OR^2$ in which $R^2$ and $R^3$ each independently is $-H$, $C_{1-4}$-alkyl or phenyl;

Y represents oxygen or sulphur;

$R^1$ represents an unsubstituted alkyl, naphthyl or phenyl group, or an alkyl, naphthyl or phenyl group substituted by one or more substituents listed for the R group;

Z represents a halogen or hydrogen;

A represents hydrogen, alkaline earth metals, alkali metals, unsubstituted ammonium or ammonium substituted by from 1 to 4 substituents selected from the group consisting of $C_{1-18}$-alkyl and phenyl, each said substituent being optionally substituted by one or more substituents listed for the R group;

y represents an integer from 0 to 8 m represents an integer from 0 to 8 n represents an integer from 0 to 32;

the sum of y and m not exceeding 8, the groups or atoms $-O-R-O-$, $-YR^1$ and Z are attached to the peripheral carbon atoms numbered 1 to 16 in Formula 2, and both of the O atoms in the $-O-R-O-$ group are bound to adjacent carbon atoms in the phthalocyanine nucleus, with the proviso that when n is zero, at least one naphthylene or phenylene group represented by R carries at least one alkyl group containing at least four carbon atoms.

11. A phthalocyanine compound according to claim 10 wherein R is a phenylene group which is unsubstituted or is substituted by one or more $C_{1-20}$-alkyl groups.

12. A phthalocyanine compound according to claim 10 or 11 wherein $R^1$ is a substituted or unsubstituted phenyl or naphthyl group.

13. A phthalocyanine compound according to claim 10 or 11 wherein A is sodium or hydrogen.

14. A phthalocyanine compound according to claim 10 or 11 wherein n is zero and each phenylene or naphthylene group represented by R carries at least one alkyl group having at least four carbon atoms.

15. A phthalocyanine compound of the formula

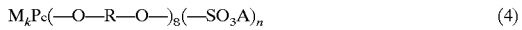

$$M_kPc(-O-R-O-)_8(-SO_3A)_n \quad (4)$$

wherein $M_kPc$, R, A and n have the meanings given in claim 1.

16. A phthalocyanine compound according to claim 15 wherein R is a phenylene group which is unsubstituted or is substituted by one or more $C_{1-20}$-alkyl groups.

17. A phthalocyanine compound according to claim 15 or 16 wherein A is sodium or hydrogen.

18. A phthalocyanine compound according to claim 15 or 16 wherein n is zero and each phenylene or naphthylene group represented by R carries at least one alkyl group having at least four carbon atoms.

19. A phthalocyanine compound according to claim 15 wherein M is selected from the group consisting of hydrogen, lithium and zinc.

* * * * *

UNITED STATES PATENT AND TRADEMARK OFFICE
CERTIFICATE OF CORRECTION

PATENT NO. : 6,335,442 B1
DATED : January 1, 2002
INVENTOR(S) : Peter Gregory et al.

It is certified that error appears in the above-identified patent and that said Letters Patent is hereby corrected as shown below:

<u>Title page,</u>
Item [73], Assignee, please correct the name to read as follows:
-- Avecia Limited, London (GB) --.

Signed and Sealed this

Twenty-seventh Day of April, 2004

JON W. DUDAS
*Acting Director of the United States Patent and Trademark Office*